(12) United States Patent
Otsuka et al.

(10) Patent No.: US 6,239,319 B1
(45) Date of Patent: May 29, 2001

(54) PROCESSES FOR THE PREPARATION OF PERFLUOROALKANES AND IODINE PENTAFLUORIDE

(75) Inventors: Tatsuya Otsuka; Tatsuya Hirata; Kyohiro Kan; Hirokazu Aoyama, all of Osaka (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 09/331,423

(22) PCT Filed: Dec. 24, 1997

(86) PCT No.: PCT/JP97/04766

§ 371 Date: Aug. 23, 1999

§ 102(e) Date: Aug. 23, 1999

(87) PCT Pub. No.: WO98/29372

PCT Pub. Date: Jul. 9, 1998

(30) Foreign Application Priority Data

Dec. 27, 1996 (JP) ..................................... 8-349374

(51) Int. Cl.[7] .................................... C07C 17/20
(52) U.S. Cl. .............................................. 570/170
(58) Field of Search ............................... 570/170

(56) References Cited

U.S. PATENT DOCUMENTS 5,482,682 * 1/1996 Tarancon .............................. 422/189
5,734,073 * 3/1998 Chambers et al. ................... 558/425

FOREIGN PATENT DOCUMENTS

| 0200908 A1 | 12/1986 | (EP) . |
| 62-005929 | 1/1987 | (JP) . |
| 09241186 | 9/1997 | (JP) . |

OTHER PUBLICATIONS

Johnson, D. E. et al. *International Journal of Chemical Kinetics*, vol. 28, pp. 43–55 (1996).

* cited by examiner

*Primary Examiner*—Johann Richter
*Assistant Examiner*—J. Parsa
(74) *Attorney, Agent, or Firm*—Birch, Stewart, Kolasch & Birch, LLP

(57) ABSTRACT

The present invention provides a new industrial process for producing perfluoroalkanes in order to overcome the problems of processes for producing perfluoroalkanes in the prior art. The process of the present invention is a process for producing a perfluoroalkane corresponding to a general formula Rf-F (wherein Rf- is a perfluoroalkyl group represented by $F(CF_2)_n$— and n is an integer of 2 to 10) by contacting a perfluoroalkyl iodide with gaseous fluorine to cause a reaction therebetween, wherein the contact is made in the presence of the liquid compound which is at least one liquid which is substantially inert to the perfluoroalkyl iodide and gaseous fluorine under the condition of the process and which is selected from a perfluoro-compound, a chlorofluoro-compound, and hydrogen fluoride.

7 Claims, 1 Drawing Sheet

PROCESSES FOR THE PREPARATION OF PERFLUOROALKANES AND IODINE PENTAFLUORIDE

This application is the national phase under 35 U.S.C. §371 of PCT International Application No. PCT/JP97/04766 which has an International filing date of Dec. 24, 1997 which designated the United States of America.

BACKGROUND OF THE INVENTION

1. Field of the Invention

The present invention relates to a process for the preparation of perfluoroalkanes, which have many applications in various fields of industries and are represented by a general formula Rf-F (wherein Rf- is a perfluoroalkyl group represented by $F(CF_2)_n$— and n is an integer of 2 to 10) and which are exemplified by perfluoroethane ($C_2F_6$) for use as a dry etching gas, a process gas in semiconductor production, and the like, perfluorohexane ($C_6F_{14}$) for use as a cleaning agent, a heat medium, and the like from the standpoint of very high stability in chemical and thermal terms, and also for the preparation of iodine pentafluoride ($IF_5$) useful as a reactive fluorinating agent or a material for intermediate products in the production of fluorine-containing compounds.

2. Description of the Prior Art

It is known to produce $C_6F_{14}$ by effecting a coupling reaction of $C_3F_7I$ as a feed material with a metal such as zinc. Disadvantages of this process are, for example, that $C_3F_7I$ for use as a feed material is difficult to obtain and that metal iodides are produced as by-products.

In general, methods known as those for producing a perfluoro-compound are as follows:

(a) electrolytic fluorination of a hydrocarbon or a halogenated hydrocarbon;

(b) fluorination of a hydrocarbon with a metal fluoride;

(c) thermal decomposition of a highly fluorinated perfluoro-compound; and (d) direct fluorination of carbon or a hydrocarbon with gaseous fluorine.

However, the above-mentioned methods are associated with, for example, the following problems.

In the method (a), since various side reactions take place and many by-products other than a target product are produced, separation/purification to obtain the target product is so difficult that the yield of the target product is remarkably reduced.

In the method (b), since many partially fluorinated products are produced, the yield of a perfluoro-compound cannot be increased.

In the method (c), a high temperature is needed for the reaction and the yield of a target product is not good.

In the method (d), there is an advantage that partially fluorinated products are hardly produced. However, gaseous fluorine is so reactive that control of reaction temperature is not easy because of vigorous heat generation involved in the reaction. As a result, C—C bonds are severed and therefore the yield of the target product decreases. In addition, since a risk of explosion and equipment corrosion accompanies the reaction, this method cannot be industrially advantageous.

Alternatively, a method in which a perfluoroalkyl iodide (Rf-I) is reacted with fluorine to obtain a perfluoroalkane and $IF_5$ is known. According to this method, however, on the one hand, the energy produced at the time of reaction is too large to amounts to about 300 kcal/mol, and on the other hand, the amount of heat being removed is too small when an ordinary heat removing means, for example, an indirect heat exchanger (such as a spiral tube, an outer jacket, and the like) which relies on the removal of sensible heat is used. Accordingly, unless the extent of the reaction itself is controlled, there is a risk that the reaction might become out of control and cause an explosion.

For example, the reaction itself between pentafluoroethyl iodide and gaseous fluorine has been reported by D. E. Johnson et al. (see International Journal of Chemical Kinetics, Vol. 28, 43–55, 1996). In order to utilize this method as an industrial method for producing pentafluoroethane and to obtain the target product in a good yield, the heat of reaction needs to be efficiently removed. However, a concrete technical means to solve the above-mentioned problem has not yet been known.

SUMMARY OF THE INVENTION

As seen from the foregoing description, the methods hitherto known for producing perfluoroalkanes are not necessarily satisfactory from the viewpoint of industrial practicality. Accordingly, it is an object of the present invention to overcome the above described disadvantages in the prior art and to provide a new method for producing perfluoroalkanes which can be industrially practical and replace the methods of prior art.

As a result of intensive studies about industrial methods for producing perfluoroalkanes such as perfluoroethane (hexafluoroethane), perfluorohexane (tetradecafluorohexane), and the like, the inventors have found that, when the above-mentioned reaction, in which a perfluoroalkyl iodide and gaseous fluorine are used to produce a perfluoroalkane and $IF_5$, is effected in the presence of the liquid which is at least one liquid which is inert to the perfluoroalkyl iodide and gaseous fluorine and has a boiling, point lower than that of $IF_5$ and which can therefore be present at least partially in a liquid phase under the reaction condition and can easily be evaporated by the heat generated by the reaction and which is selected from a perfluoro-compound, a chlorofluoro-compound, and hydrogen fluoride, the huge amount of heat generated by the reaction may be absorbed/removed as latent heat required for the evaporation of the above-mentioned at least one liquid, which is selected from a perfluoro-compound, a chlorofluoro-compound, and hydrogen fluoride, so that the reaction temperature may be easily and efficiently controlled.

Consequently, since the reaction temperature can be prevented from being excessively high, that is, the reaction temperature can be controlled as desired, side reactions can be inhibited. In addition, since conventionally employed equipment for indirectly cooling the reaction liquid to remove the heat of reaction may be omitted, the reaction equipment as a whole becomes simple and economically advantageous.

Moreover, there is an advantage that $IF_5$, which is produced simultaneously from the reaction, can be used as a starting material for the production of, for example, a perfluoroalkyl iodide.

Accordingly, the present invention provides a process for producing a perfluoroalkane corresponding to a general formula Rf-F (wherein Rf- is a perfluoroalkyl group represented by $F(CF_2)_n$— and n is an integer of 2 to 10) by contacting a perfluoroalkyl iodide with gaseous fluorine so as to react them, characterized in that the contact is made in the presence of at least one liquid compound selected from a perfluoro-compound, a chlorofluoro-compound, and hydrogen fluoride which liquid compound is substantially inert to the perfluoroalkyl iodide and gaseous fluorine under conditions of the process.

The term "substantially inert" as used herein means that a compound is inert such that it does not exert an adverse influence which offsets the advantages obtainable by performing the process of the present invention. In other word, it means that a compound is substantially inert vie to a reaction in which a perfluoroalkane and $IF_5$ are produced and therefore the compound does not exert on the reaction an adverse influence that overrides the advantage obtainable by the present invention.

DETAILED DESCRIPTION OF THE PRESENT INVENTION

Figure 1:
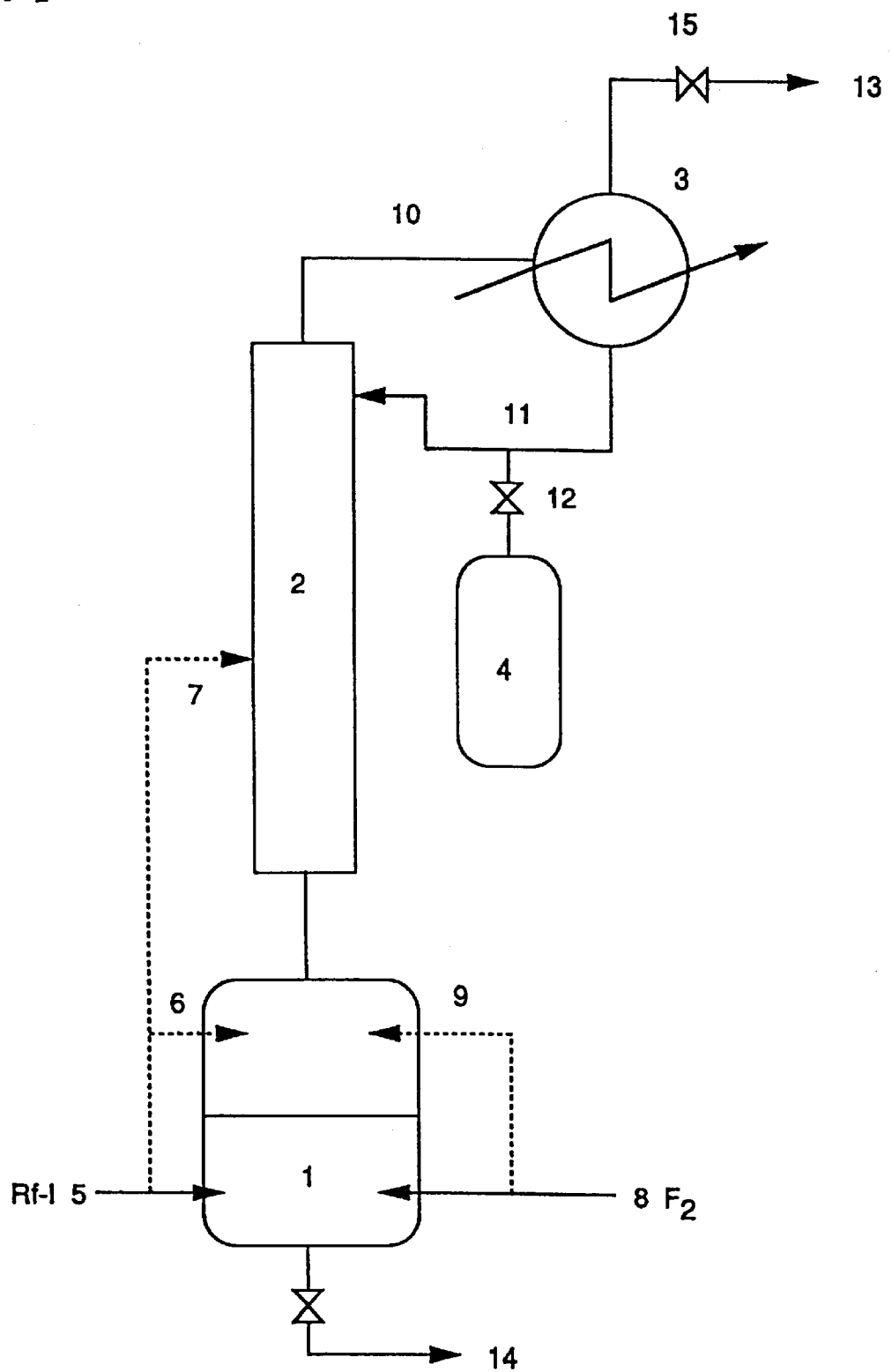
FIG. 1 is a schematically illustrated flow sheet of the equipment in which the process of the present invention is carried out. In this drawing, a reference numeral 1 designates a reaction vessel; a reference numeral 2 designates a tower zone; a reference numeral 3 designates a condenser; a reference numeral 4 designates a receiver; and reference numerals 12 and 15 designate valves, respectively.

In the present invention, the contact between a perfluoroalkyl iodide with gaseous fluorine can be made in any way so long as the two components are simultaneously present to react with each other (for example, the contact for reaction can be made by introducing the gaseous fluorine into the perfluoroalkyl iodide), wherein at least one liquid which is selected from a perfluoro-compound, a chlorofluoro-compound, and hydrogen fluoride is present. For example, in order to promote the reaction and the removal of heat of reaction in the presence of the above-mentioned liquid and to accelerate the contact of the two reactants with the liquid, a positive mixing operation may be conducted such that all of the components are mechanically mixed (for example, by stirring), or a mild mixing operation may be conducted such that the two reactants and the liquid flow inside a suitable gas-liquid or liquid-liquid contact apparatus such as a plate tower or a packed tower. More concretely, the following modes can be listed as examples.

A mode in which a perfluoroalkyl iodide as a liquid phase and gaseous fluorine are supplied into at least one liquid selected from a perfluoro-compound, a chlorofluoro-compound, and hydrogen fluoride (wherein mechanical mixing may or may not be employed);

A mode in which a perfluoroalkyl iodide as a gas phase and gaseous fluorine are supplied into at least one liquid selected from a perfluoro-compound, a chlorofluoro-compound, and hydrogen fluoride (wherein mechanical mixing may or may not be employed);

A mode in which a perfluoroalkyl iodide as a liquid phase and gaseous fluorine are supplied adjacent to the liquid phase of at least one liquid selected from a perfluoro-compound, a chlorofluoro-compound, and hydrogen fluoride;

A mode in which a perfluoroalkyl iodide as a gas phase and gaseous fluorine are supplied adjacent to the liquid phase of at least one liquid selected from a perfluoro-compound, a chlorofluoro-compound, and hydrogen fluoride; and A mode comprised of a combination of the above-described modes.

As an example of the mode in which supply is made adjacent to the liquid phase, the reactants may be supplied (without employing positive mechanical mixing) adjacent to the flowing-down phase of at least one liquid selected from a perfluoro-compound, a chlorofluoro-compound, and hydrogen fluoride (simply supplied into flowing-down phase). In this case, the reactants may be supplied in a countercurrent flow or in a parallel current flow with respect to the flowing-down phase of the liquid. Specifically, this mode corresponds to a mode in which liquid or gaseous reactants are supplied to a packed tower wherein at least one liquid selected from a perfluoro-compound, a chlorofluoro-compound, and hydrogen fluoride flows down inside thereof. Needless to say, even without employing positive mechanical mixing, the presence of the packing enables gas-liquid and/or liquid-liquid contact so that the reactants and the liquid are naturally mixed with each other.

According to the process of the present invention, the reaction which can be caused by the contact is expressed mainly by the formula:

$$Rf\text{-}I + 3F_2 \rightarrow Rf\text{-}F + IF_5 \qquad (1)$$

(wherein Rf- is the same as defined above.)

Accordingly, the present invention provides a process for producing a perfluoroalkane corresponding to a general formula Rf-F, wherein the reaction:

$$Rf\text{-}I + 3F_2 \rightarrow Rf\text{-}F + IF_5 \qquad (1)$$

(wherein Rf- is the same as defined above) is effected in the presence of at least one liquid selected from a perfluoro-compound, a chlorofluoro-compound, and hydrogen fluoride which liquid is substantially inert to the perfluoroalkyl iodide and gaseous fluorine and evaporates at least partially by heat generated by the reaction.

In the process of the present invention, the heat generated by a reaction, for example, the reaction indicated by the formula (1), is used for the evaporation of at least one liquid selected from a perfluoro-compound, a chlorofluoro-compound, and hydrogen fluoride which liquid is present as a liquid in the reaction system. The compound evaporated from at least one liquid selected from a perfluoro-compound, a chlorofluoro-compound, and hydrogen fluoride is taken out of the reaction system and thereafter cooled and condensed in a conventionally employed condenser. In this way, the heat of reaction may be removed from the reaction system. The term "reaction system" is used in the present invention to mean a region in such a state that the reactants are existing and the reaction may occur or the reaction actually occurs, or alternatively, a region including both of these states. In the present invention, the evaporated compound may be condensed after being taken out of the reaction system or the evaporated compound may be condensed in the reaction system.

In comparison with indirect heat exchange conventionally employed for the removal of heat from a reaction system, the above-described method for removing heat of reaction by using latent heat of evaporation is advantageous from the following viewpoints. That is, the heat can be removed directly from the reaction system; and a large amount of heat can be removed by a small amount of liquid which is at least one liquid selected from a perfluoro-compound, a chlorofluoro-compound, and hydrogen fluoride because the heat is removed not as sensible heat but as latent heat. The condensed liquid which is at least one liquid selected from a perfluoro-compound, a chlorofluoro-compound, and hydrogen fluoride, may be returned to the reaction system so that the liquid is used again for the removal of heat.

In the present invention, the liquid compound which is at least one liquid selected from a perfluoro-compound, a chlorofluoro-compound, and hydrogen fluoride, is not particularly limited so long as the it is a compound substantially inert to gaseous fluorine under the reaction condition, capable of existing as a liquid phase in the reaction system, and capable of being evaporated by the heat generated by the reaction. These compounds may be used alone or alternatively may be used in a combination of two or more of them with the proviso that such a combination does not cause a serious industrial disadvantage.

Examples of compounds usable as the above-described at least one liquid selected from a perfluoro-compound, a chlorofluoro-compound, and hydrogen fluoride may include the following compounds:

(a) perfluoro- or chlorofluoroalkanes (such as perfluoroethane, perfluoropropane, perfluorobutane, perfluorohexane, dichlorodifluoromethane, trichlorotrifluoroethane, fluorotrichloromethane, dichlorotetrafluoroethane, and the like), (b) perfluorocycloalkanes (such as perfluorocyclobutane, perfluorocyclopentane, perfluorocyclohexane, perfluorodecalin, and the like), and (c) perfluoroamines (such as perfluorotributylamine, perfluorotriethylamine, and the like). Preferably, each of these compounds has 1 to 15 carbon atoms.

Among these perfluoro-compounds and chlorofluoro-compounds, particularly preferred compounds have a relatively low boiling point (under atmospheric pressure), for example, of 100° C. or below, in particular in a range from −40 to 80° C., and which include compounds having 1 to 7 carbon atoms. Since these compounds easily evaporate, they may be advantageously used for removal of the heat of reaction.

The compounds to be concretely used are preferably selected by taking into account the reaction condition in which a target perfluoroalkane is prepared. Generally, the difference in boiling point between the perfluoroalkane as a target product and at least one liquid selected from a perfluoro-compound, a chlorofluoro-compound, and hydrogen fluoride is not so important, and, therefore, whichever of them may have a higher boiling point. For example, when the perfluoroalkane has a higher boiling point, the target product alone may be advantageously retained in the reaction system, but the liquid compound which is at least one liquid selected from a perfluoro-compound, a chlorofluoro-compound, and hydrogen fluoride is evaporated from the reaction system and recycled after being condensed to the reaction system. To the contrary, when the boiling point of the perfluoroalkane is lower than or close to that of the liquid compound which is at least one liquid selected from a perfluoro-compound, a chlorofluoro-compound, and hydrogen fluoride, all of the perfluoroalkane and the liquid compound which is at least one liquid selected from a perfluoro-compound, a chlorofluoro-compound, and hydrogen fluoride, may be taken out of the reaction system by evaporation and then condensed, and thereafter, the condensate may be subjected to a separating operation such as rectification or liquid separation so that only the liquid compound which is at least one liquid selected from a perfluoro-compound, a chlorofluoro-compound, and hydrogen fluoride may be returned to the reaction system. In this case, there is an advantage that the target product can also be separated. Naturally, the both fractions may also be recycled without being separated each other.

According to a particularly preferable mode of the present invention, a perfluoroalkane, which is a target product, is utilized as a perfluoro-compound to be evaporated by the heat of reaction. In this mode, since the perfluoroalkane alone evaporates from the reaction system to the outside, the evaporated perfluoroalkane is condensed by cooling and then a necessary amount thereof is returned to the reaction system. Therefore, an advantage of this mode is that the above-described separation after condensation may be omitted. Another advantage of this mode is that a third component is not mingled into the reaction system. For example, in the preparation of $C_6F_{14}$, the heat of reaction may be removed by using the $C_6F_{14}$ as a perfluoro-compound. According to another example, $C_4F_{10}$ can be used for the preparation of $C_4F_{10}$.

According to the process of the present invention, in the presence of the above-described the liquid compound which is at least one liquid which is selected from a perfluoro-compound, a chlorofluoro-compound, and hydrogen fluoride, contact between a perfluoroalkyl iodide and gaseous fluorine is made so that the above-described reaction (1) is effected. The condition of the contact or reaction is an ordinary one and is not particularly limited.

The reaction condition may be appropriately selected depending on the perfluoroalkane which is a target product and on the liquid compound which is at least one liquid selected from a perfluoro-compound, a chlorofluoro-compound, and hydrogen fluoride to be used in the reaction. In a specific example, a reaction condition comprising a temperature in a range from −50 to 100° C. and a pressure in a range from atmospheric pressure (or a reduced pressure in some cases) to 5 $Kg/cm^2$-G may be exemplified. As to the reaction temperature, it is preferable to maintain the reaction temperature substantially equal to the boiling point of the liquid compound which is at least one liquid selected from a perfluoro-compound, a chlorofluoro-compound, and hydrogen fluoride under the reaction condition by using the liquid compound which is at least one liquid selected from a perfluoro-compound, a chlorofluoro-compound, and hydrogen fluoride in an amount sufficient to allow it evaporate by absorbing the heat of reaction. In this case, there is an advantage that the reaction temperature can be maintained constant at the boiling point.

The amounts of a perfluoroalkyl iodide and gaseous fluorine to be contacted with each other for reaction are not particularly limited. However, in order to obtain the perfluoroalkane efficiently, it is preferable to use the gaseous fluorine in an amount more than a stoichiometric amount (namely, 3 or more moles of gaseous fluorine per 1 mole of perfluoroalkyl iodide). An optimum amount of gaseous fluorine is generally 3 to 5 molar times the amount of perfluoroalkyl iodide. The unreacted excessive gaseous fluorine leaves from the reaction system in the form of a gas together with the liquid compound which is at least one liquid selected from a perfluoro-compound, a chlorofluoro-compound, and hydrogen fluoride and optionally together with the target product which evaporate. Therefore, the use of the gaseous fluorine in a large excess amount is not economical because a large-scale apparatus is needed for the recovery of the unreacted gaseous fluorine and the recycle thereof.

In the process of the present invention, the liquid compound which is at least one liquid selected from a perfluoro-compound, a chlorofluoro-compound, and hydrogen fluoride as well as a perfluoroalkane which is optionally present and is a target reaction product, are generally taken out of the reaction system ordinarily by evaporation. As a result of subsequent cooling and condensation of the vapor, the heat of reaction is taken out of the reaction system. For the cooling and condensation, any type of conventional condensers may be used. In such a case where the target product is also evaporated and where the difference in boiling point between the perfluoroalkane and that of the liquid compound which is at least one liquid selected from a perfluoro-compound, a chlorofluoro-compound, and hydrogen fluoride is large, condensation and separation are advantageously performed simultaneously by fractional condensation (or partial condensation). Needless to say, total condensation rather than fractional condensation is also possible so that separation is later conducted in an ordinary manner by, for example, rectification.

In the case where the process of the present invention is carried out on a batch basis, an embodiment thereof is as follows. Predetermined amounts of a perfluoroalkyl iodide and of the liquid compound which is at least one liquid selected from a perfluoro-compound, a chlorofluoro-compound, and hydrogen fluoride are placed in a reaction vessel, and thereafter a predetermined amount of gaseous fluorine is added to the reaction system. Then, the liquid compound which is at least one liquid selected from a perfluoro-compound, a chlorofluoro-compound, and hydrogen fluoride as well as, optionally, a perfluoroalkane are taken out of the reaction system by evaporation as the reaction proceeds and then condensed. The total amount of the condensate is returned to the reaction system and is used for the removal of the heat of a subsequent reaction. In some cases, it is also possible to return only the liquid compound which is at least one liquid selected from a perfluoro-compound, a chlorofluoro-compound, and hydrogen fluoride to the reaction system after the target product is separated from the condensate.

Since the boiling point of $IF_5$, which is formed at the same time, is 104.5° C., $IF_5$ accumulates in the reaction system if the boiling point of the inert liquid (a perfluoro-compound or a chlorofluoro-compound) provided to the reaction is lower than 104.5° C. Naturally, depending on the apparatus to be used and operational condition to be employed, a small amount of $IF_5$ may be entrained in an evaporating compound. For example, at a point, where a predetermined reaction is completed, the supply of gaseous fluorine is stopped and the target product and the liquid which is at least one liquid selected from a perfluoro-compound, a chlorofluoro-compound, and hydrogen fluoride are taken out of the reaction system by distillation and condensation. Then, by employing an ordinary means (for example, rectification), a perfluoroalkane is separated from the liquid which is at least one liquid selected from a perfluoro-compound, a chlorofluoro-compound, and hydrogen fluoride. After being purified as necessary, the perfluoroalkane becomes a final product. $IF_5$ formed as a by-product remains in the reaction system as a residue together with, for example, the rest of the liquid which is at least one liquid selected from a perfluoro-compound, a chlorofluoro-compound, and hydrogen fluoride. Therefore, $IF_5$ can be separated and recovered by taking out the residue and treating the residue by an ordinary method such as distillation.

In the case where the process of the present invention is carried out continuously, an embodiment thereof is as follows. At least one liquid selected from a perfluoro-compound, a chlorofluoro-compound, and hydrogen fluoride is placed in a reaction vessel, and, if necessary, the liquid is heated to a predetermined temperature. Then, a perfluoroalkyl iodide and gaseous fluorine as reactants are continuously supplied to the reaction vessel. By the heat generated in the reaction, the liquid which is at least one liquid selected from a perfluoro-compound, a chlorofluoro-compound, and hydrogen fluoride as well as the target product are taken out of the reaction system by evaporation and then condensed by cooling. The condensate is continuously separated such that the liquid which is at least one liquid selected from a perfluoro-compound, a chlorofluoro-compound, and hydrogen fluoride is returned to the reaction system, while the perfluoroalkane is continuously recovered as a final product. Alternatively, the reaction system (liquid) may be continuously extracted and $IF_5$ may be separated and recovered from the extracted liquid. The residual liquid may be returned to the reaction system.

In the case where the process of the present invention is carried out on a continuous basis, another embodiment thereof is as follows. The liquid which is at least one liquid selected from a perfluoro-compound, a chlorofluoro-compound, and hydrogen fluoride is placed in a reaction vessel and is distilled by heating. Then, by returning the distillate after condensation to the reaction vessel, a refluxing state of the foregoing compound is formed. Next, in the presence of the compound flowing down toward the reaction vessel, a perfluoroalkyl iodide and gaseous fluorine are continuously supplied to the reaction vessel. In one example, they may be added to the compound flowing down. In another example, a perfluoroalkyl iodide is added to the compound flowing down, or alternatively, a perfluoroalkyl iodide is not added to the compound flowing down but is allowed to flow down co-currently adjacent to the compound flowing down, wherein gaseous fluorine may be supplied countercurrently. In this case, while the liquid which is at least one liquid selected from a perfluoro-compound, a chlorofluoro-compound, and hydrogen fluoride flows down, the reaction proceeds in the compound, so that a part of the compound is evaporated by the heat of reaction and the target product is also evaporated in some cases. Therefore, it is possible to create a state where the liquid which is at least one liquid selected from a perfluoro-compound, a chlorofluoro-compound, and hydrogen fluoride as well as $IF_5$ are substantially present in the reaction vessel.

The equipment for carrying out the process of the present invention comprises a reaction vessel for accommodating the reaction system and a condenser for condensing the vapor of the liquid which is at least one liquid selected from a perfluoro-compound, a chlorofluoro-compound, and hydrogen fluoride being evaporated from the reaction system as well as the vapor of the target product also being evaporated in some cases. In a preferred mode, the equipment comprises, for example, a tower zone provided above the reaction vessel such as a packed tower zone as an intermediate element between a still constituting the reaction vessel and the condenser. In such equipment, gaseous fluorine can be continuously supplied to the still and a perfluoroalkyl iodide as a reactant can be continuously supplied to the packed tower zone so that the reaction proceeds in the packed tower zone. Alternatively, as described above, both of the gaseous fluorine and perfluoroalkyl iodide may be supplied to the tower zone. In this case, the heat of reaction in the packed tower zone can be removed by returning the condensate from the condenser to the packed tower zone. The construction of the tower zone is not limited to a packed tower type. Constructions for use as a fractional distillation tower in general, such as an OlderShaw type, a bubble cap type, a sieve tray type, and the like, may be used.

According to the process of the present invention, in general, a perfluoroalkyl iodide may be supplied as a liquid or as a gas. According to the process of the present invention, naturally, $IF_5$ is also formed at the same time, and therefore, IF$_5$ can also be obtained in an industrially economical way. In the case where IF$_5$ is dissolved in a liquid inside the still, IF$_5$ can be recovered by evaporating the other liquid component. In the case where IF$_5$ is not dissolved in a liquid inside the still, that is, IF$_5$ is present as a solid or a liquid as a separated phase, IF$_5$ can be recovered by a suitable solid-liquid or liquid-liquid separating method, such as filtration or decantation, or it can be simply separated and recovered by an ordinary fractional distillation or the like.

In one specific example of preferable modes of the present invention, by using perfluoroethyl iodide as a perfluoroalkyl iodide and octafluorocyclobutane as a perfluoro-compound and/or hydrogen fluoride, perfluoroethane is obtained by reacting perfluoroethyl iodide with gaseous fluorine under, for example, a refluxing condition in the presence of the octafluorocyclobutane and/or hydrogen fluoride. In this mode, by using reaction equipment comprising a still and a tower zone provided thereon, the tower zone can be cooled with, for example, brine. In this arrangement, substantially only the reaction product in the form of a vapor can be taken out of the reaction equipment by condensing evaporated octafluorocyclobutane and/or hydrogen fluoride as a result of cooling of the tower zone. By cooling the reaction product thus taken out in the form of a vapor, perfluoroethane as a target product can be obtained.

Since IF$_5$ accumulates in the still, a portion of the liquid may be continuously or intermittently taken out, and after IF$_5$ is recovered therefrom, the rest of the liquid may be returned to the still. Alternatively, IF$_5$ is allowed to accumulate in the still until completion of the reaction so that IF$_5$ is recovered from the liquid in the still after completion of the reaction.

In another specific example of preferable modes of the present invention, by using perfluorohexyl iodide as a perfluoroalkyl iodide, perfluorohexane is formed and the perfluorohexane which is the target product is used as a perfluoro-compound. In this case, substantially only perfluorohexane evaporates by the heat of reaction and thus the heat of reaction can be substantially removed. On a continuous basis, perfluorohexane in an amount corresponding to the amount of perfluorohexyl iodide supplied to the reaction system (accordingly an amount corresponding to the amount of perfluorohexane to be formed) is recovered from condensate and the rest is returned as reflux to the reaction system. On a batch basis, the reaction is continued in a complete refluxing state.

In the process of the present invention, gaseous fluorine may be diluted with a gas inert to the reaction. Examples of usable inert gas include nitrogen, helium, tetrafluoromethane, and the like. However, when other component is added, the separation/removal thereof comes to be required. Therefore, in some cases, it may be preferable to use as a diluent the target product of the present invention or the liquid which is at least one liquid selected from a perfluoro-compound, a chlorofluoro-compound, and hydrogen fluoride. The dilution of gaseous fluorine brings about an advantage that the gaseous fluorine can be prevented from being localized in a perfluoroalkyl iodide and the contact therebetween can be made more uniform.

In the process of the present invention, the recovered IF$_5$ can be used to form perfluoroethyl iodide according to, for example, the following reaction:

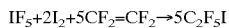

$C_2F_5I$ thus formed can be used in the reaction (1). This compound can also be used for the formation of various perfluoroalkyl iodides such as $C_6F_{13}I$ as shown in the reaction formula as follows:

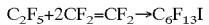

Referring now to the drawings, the process of the present invention will be explained in more details.

FIG. 1 is a schematically illustrated flow sheet of the equipment which can be used for the process of the present invention. The equipment used in Examples is substantially the same as this equipment. The illustrated equipment comprises a reaction vessel 1, a tower zone (for example, a packed tower) 2, a condenser 3, and a receiver 4.

The contact between a perfluoroalkyl iodide and gaseous fluorine takes place in the reaction vessel 1 and/or the tower zone 2. Since heat of reaction is generated in the place of contact, at least one compound selected from a perfluoro-compound, a chlorofluoro-compound, and hydrogen fluoride is present as a liquid phase in the reaction vessel 1 and/or the tower zone 2. The compound evaporated is then cooled by a condenser 3. In this way, the heat of reaction is removed by the compound.

A tower zone 2 is not necessarily to be in the shape of a tower. It may be in any shape so long as the contact and mixing of the reactants of the present invention are possible and further the heat removal can be performed by the liquid which is at least one compound selected from a perfluoro-compound, a chlorofluoro-compound, and hydrogen fluoride.

A perfluoroalkyl iodide (Rf-I) can be supplied through the line 5. The supply may be on a batch basis or on a continuous basis. The supply site may be any of the reaction vessel 1 and the tower zone 2. Besides the line 5 to the liquid phase inside the reaction vessel 1, at least one supply route can be selected from the line 6 to the gaseous phase of the reaction vessel 1, the line 7 to the tower zone 2, and others. In the case where a perfluoroalkyl iodide is supplied continuously, if the perfluoroalkyl iodide has a boiling point lower than the lowest boiling point of the liquid which is at least one compound selected from a perfluoro-compound, a chlorofluoro-compound, and hydrogen fluoride, the perfluoroalkyl iodide is preferably supplied to the reaction vessel 1. In this case, the line 5 or 6 is used. On the other hand, if the perfluoroalkyl iodide to be supplied has a boiling point higher than the highest boiling point of the liquid which is at least one compound selected from a perfluoro-compound, a chlorofluoro-compound, and hydrogen fluoride, the perfluoroalkyl iodide is preferably supplied to the tower zone 2. In this case, the line 7 is used.

Gaseous fluorine can be supplied continuously through the line 8 to the liquid phase part of the reaction vessel 1. It may also be supplied through the line 9 to the vapor phase part of the reaction vessel 1. Further, if necessary, it may also be supplied to the tower zone 2.

At least one liquid compound selected from a perfluoro-compound, a chlorofluoro-compound, and hydrogen fluoride may be supplied to the reaction vessel 1 and/or the tower zone 2 prior to or concurrently with the reaction between the perfluoroalkyl iodide and gaseous fluorine. Since none of these liquid compounds is involved in the reaction, basically the mere presence of a predetermined amount of them meets the purpose unless they are lost from the reaction system.

The gaseous phase created by vaporization in the reaction vessel 1 and/or the tower zone 2 is introduced through the line 10 into the condenser 3. The condensate in whole or in part, as necessary, is returned through the line 11 to the tower zone 2. Where part of the condensate is returned, the rest is introduced into a receiver 4. The rest thus obtained may be, for example, a perfluoroalkane as a target product. Meanwhile, based on the relationship between boiling points of a perfluoroalkane (Rf-F) formed and other accompanying compounds, the perfluoroalkane (Rf-F) can be recovered as an uncondensed gas through the line 13 from the top of the condenser 3. As necessary, the uncondensed gas may be liquefied in a subsequent treatment for recovery.

The liquid in the reaction vessel 1 may be taken out through the line 14 to recover the formed IF, intermittently or continuously. Alternatively, such treatment may be made upon completion of the reaction.

The pressure inside the reaction equipment can be controlled by, for example, adjusting the opening of a valve 15.

INDUSTRIAL APPLICABILITY

According to the process of the present invention, by performing a reaction by contacting a perfluoroalkyl iodide, such as perfluoroethyl iodide, perfluorohexyl iodide, and the like, with gaseous fluorine in the presence of the liquid which is at least one liquid selected from a perfluoro-compound, a chlorofluoro-compound, and hydrogen fluoride, for example, in the presence of perfluorocyclobutane, hydrogen fluoride and/or perfluorohexane, and the like, heat of reaction can be efficiently absorbed and therefore the reaction temperature can be easily controlled. Consequently, a perfluoroalkane, such as perfluoroethane, perfluorohexane, and the like, can be obtained in a high selectivity, and iodine pentafluoride is also obtained at the same time.

EXAMPLES

Example 1

A wide-mouthed bottle, which was made of a fluororesin (PFA) and had an inner capacity of 500 mL, was used as the reaction vessel 1. A fluoro-rubber stopper was provided to the vessel and holes were made in the stopper so that a tower zone and a feed material supply line were connected through the holes.

A stainless steel (SUS 316) tube (having an outer diameter of ⅝ inch and a length of 1000 mm) was used as the tower zone 2. An upper portion in 500 mm of the SUS tube constituting the tower zone 2 was used as the condenser 3 by providing a cooling jacket to the tube. A cooling medium having a temperature of −20° C. was flown to cool the condenser zone. The interior of the tower was packed with Hastelloy C mesh.

Octafluorocyclobutane (500 g) and $C_2F_5I$ (30 g) were charged into the reaction vessel 1 and heated to a complete refluxing state. Then, while the liquid inside the reaction vessel was being stirred, gaseous fluorine diluted to a concentration of 30% by weight with nitrogen was introduced into the reaction vessel through the line 8 at a rate of 75 Ncc/minute.

The reaction was effected under a normal pressure. During the reaction, the liquid inside the reaction vessel was in a boiling state and was kept at a constant temperature of −5° C. The reaction was continued for 7 hours. During the reaction, the octafluorocyclobutane evaporated by the heat of reaction was cooled/condensed inside the tower serving as the condenser 3 and was allowed to flow down inside the tower. The uncondensed gas discharged from the top of the condenser 3 was extracted from the line 13 (in this example, the line used as the line 10 was common to the line 11, and a receiver 4 was not used). The gas thus extracted was passed through a mixture of an alkali and a reducing agent to eliminate by absorption the unreacted gaseous fluorine entrained in perfluoroethane and was then dried and recovered by means of a tube packed with calcium chloride.

The gas obtained was analyzed by means of gas chromatography, as a result, it was found that the purity of perfluoroethane was 99 mole % or more. Upon completion of the reaction, octafluorocyclobutane was distilled off from the liquid in the reaction vessel to thereby obtain a residue. After analysis, the residue was found to be $IF_5$ having a purity of 99 mole % or more.

Example 2

As in Example 1, 500 g of octafluorocyclobutane was charged into the reaction vessel and heated to a refluxing state. Then, while the liquid was being stirred, $C_2F_5I$ in a gaseous state was introduced into the reaction vessel through the line 5 at a rate of 6 Ncc/minute. At the same time, gaseous fluorine diluted to a concentration of 30% by weight with nitrogen was introduced into the reaction vessel through the line 8 at a rate of 75 Ncc/minute.

After effecting the reaction for 7 hours, analysis was conducted. As a result, the gas obtained as an uncondensed gas was found to include 99 mole % or more of perfluoroethane and the residue in the reaction vessel was found to include 99 mole % or more of $IF_5$.

Example 3

The reaction was effected using equipment generally called rectifying equipment.

A still (made of SUS 316 and having a capacity of 1L) having a rectifying column was used as the reaction vessel 1. A rectifying column 2 (made of SUS 316, 25A1200 mm, packed with SUS packing of 20 theoretical plate number) was used as the tower zone 2. An SUS 316 condenser (having a heat transfer area of 0.1 m$^2$) was used as the condenser 3.

850 g of anhydrous hydrofluoric acid (hydrogen fluoride) was charged into the reaction vessel 1 and heated to reflux under atmospheric pressure, while a cooling medium having a temperature of −20° C. was flown in the condenser 3.

Then, gaseous fluorine (having a concentration of 100%) was supplied through the line 8 at a flow rate of 300 Ncc/minute to the liquid phase part of anhydrous hydrofluoric acid in the reaction vessel, and pentafluoroethyl iodide ($C_2F_5I$) gas was charged through the line 6 at a flow rate of 100 Ncc/minute to the vapor phase part in the reaction vessel. In this way, the reaction was effected.

The uncondensed gas discharged from the top of the condenser 3 was introduced through the line 13 into a cleaning tower (not shown) to wash the gas with an aqueous solution containing a mixture of potassium hydroxide and potassium sulfite. After being washed and dried, the gas was analyzed by means of gas chromatography, as a result, it was found that the conversion of pentafluoroethyl iodide was 100% and the selectivity for hexafluoroethane was 98.8%.

The reaction was continued for 3 hours, and then, the supply of gaseous feed material was terminated and anhydrous hydrofluoric acid was subjected to rectification and recovered in the receiver 4. By the rectification of the liquid remaining in the reaction vessel, $IF_5$ was obtained.

Example 4

The same reaction equipment as in Example 3 was used.

1,017 g of octafluorocyclobutane was charged into the reaction vessel 1 and heated to reflux, while a cooling medium having a temperature of −20° C. was flown in the condenser 3. The pressure inside the tower was controlled by means of a pressure control valve 15 so that the temperature of the still was kept at about 10° C. (0.4 to 1.5 KG in gauge pressure).

Then, gaseous fluorine (having a concentration of 100%) was supplied through the line 8 at a flow rate of 30 Ncc/minute to the liquid phase part of octafluorocyclobutane in the reaction vessel, and gaseous pentafluoroethyl iodide ($C_2F_5I$) was supplied through the line 7 at a flow rate of 10 Ncc/minute to almost the longitudinal middle section of the rectifying tower 2.

The uncondensed gas discharged from the top of the condenser 3 was introduced through the line 13 into an alkali-cleaning tower (not shown) to wash the gas with an aqueous solution containing a mixture of potassium hydroxide and potassium sulfite. After being washed and dried, the gas was analyzed by means of gas chromatography, as a result, it was found that the conversion of pentafluoroethyl iodide was 100% and the selectivity for hexafluoroethane was 99.2%.

Example 5

The same reaction equipment as in Example 3 was used.

860 g of octafluorocyclobutane was charged into the reaction vessel 1 and heated to reflux under atmospheric pressure, while a cooling medium having a temperature of 20° C. was flown in the condenser 3.

Then, gaseous fluorine (having a concentration of 100%) was supplied through the line 8 at a flow rate of 34 Ncc/minute to the liquid phase part of octafluorocyclobutane in the reaction vessel, and gaseous pentafluoroethyl iodide ($C_2F_5I$) was charged through the line 7 at a flow rate of 10 Ncc/minute. The uncondensed gas discharged from the top of the condenser 3 was introduced through the line 13 into an alkali-cleaning tower (not shown) to wash the gas with an aqueous solution containing a mixture of potassium hydroxide and potassium sulfite. After being washed and dried, the gas was analyzed by means of gas chromatography, as a result, it was found that the conversion of pentafluoroethyl iodide was 100% and the selectivity for hexafluoroethane was 98.9%.

Example 6

A wide-mouthed bottle, which was made of a fluororesin resin (PFA) and had an inner capacity of 750 mL, was used as the reaction vessel 1. A fluoro-rubber stopper was provided to the vessel and holes were made in the stopper so that a tower zone was connected. As the tower zone 2, a PFA tube (having an outer diameter of 1 inch and a length of 270 mm) was used, which tube was packed with PFA tubes each cut into a size having an outer diameter of ¼ inch and a length of about 7 mm. A jacketed PFA tube (having an outer diameter of 1 inch and a length of 300 mm) was used as the condenser 3 and was cooled by flowing a cooling medium having a temperature of −20° C. As the connecting line 11 between the condenser 3 and the tower zone 2, a piping joint made of SUS was used. A PFA bottle having a capacity of 500 mL was used as the receiver 4, which was connected to the line 11 via a valve 12. The line 7 for charging a perfluoroalkyl iodide as a feed material was connected to the line 11.

300 g of perfluorohexane was charged into the reaction vessel 1 and heated to form a total reflux state by means of a water bath. The temperature inside the tower zone and the reaction vessel 1 were raised to 57° C. Then, $C_6F_{13}I$ was charged into the uppermost part of the tower zone 2 through the line 7 at a rate of 89 mg/minute. At the same time, gaseous fluorine diluted to a concentration of 20% by weight with nitrogen was introduced into the reaction vessel through the line 9 at a rate of 100 Ncc/minute.

During the reaction, the perfluorohexane evaporated by the heat of reaction was allowed to be cooled/condensed inside the tower of the condenser 3 and to flow down inside the tower zone. $C_6F_{14}$ in an amount corresponding to the charged amount of $C_6F_{13}I$ was recovered in the receiver 4 through the line 11. The uncondensed gas discharged from the top of the condenser 3 was extracted from the line 13 (in this example, the line used as the line 10 was common to the line 11). The uncondensed gas thus extracted was passed through a mixture of an alkali and a reducing agent to eliminate by absorption the unreacted gaseous fluorine entrained in gaseous nitrogen.

The reaction was effected under a normal pressure. During the reaction, the liquid in the reaction vessel was in a boiling state and the temperature thereof was at a constant temperature of 57° C. The reaction was effected for 11 hours.

The residue in the reaction vessel 1 separated into two layers of $IF_5$ and $C_6F_{14}$. The contents of the reaction vessel 1 and the receiver 4 were analyzed by means of gas chromatography, as a result, it was found that the conversion of $C_6F_{13}I$ was 96% and the selectivity for $C_6F_{14}$ was 95%.

According to gas chromatography analysis of the uncondensed gas, no decomposition product was found.

Example 7

The same reaction equipment as in Example 6 was used to carry out a reaction. 100 g of perfluorohexane was charged into the reaction vessel 1 and heated to reflux. Then, $C_6F_{13}I$ as a feed material was supplied from the top of the tower zone through the line 7 at a rate of 92 mg/minute. At the same time, gaseous fluorine diluted to a concentration of 20% by weight with gaseous perflurohexane was introduced into the reaction vessel through the line 9 at a rate of 100 Ncc/minute.

As in Example 6, the reaction was effected for 10 hours at 57° C. The contents of the reaction vessel 1 and the receiver 4 were analyzed by means of gas chromatography, as a result, it was found that the conversion of $C6F_{13}I$ was 97% and the selectivity for $C_6F_{14}$ was 95%.

Example 8

The same reaction equipment as in Example 6 was used to carry out a reaction. 400 g of octafluorocyclobutane was charged into the reaction vessel 1 and heated to reflux. Then, $C_6F_{13}I$ as a feed material was supplied from the top of the tower zone through the line 7 at a rate of 45 mg/minute. At the same time, gaseous fluorine diluted to a concentration of 10% by weight with nitrogen was introduced into the reaction vessel through the line 9 at a rate of 100 Ncc/minute.

During the reaction, the octafluorocyclobutane evaporated by the heat of reaction was cooled/condensed by the condenser 3. All of the condensate was returned through the line 11 to the tower zone 2 (in this example, the line used as the line 10 was common to the line 11, and a receiver 4 was not used). The uncondensed gas discharged from the top of the condenser 3 was extracted from the line 13. The uncondensed gas was recovered by absorptive separation.

The reaction was effected under a normal pressure. During the reaction, the liquid inside the reaction vessel was in a boiling state and was kept at a constant temperature of −5° C. The reaction was effected for 5 hours The residue in the reaction vessel 1 separated into two layers of an octafluorocyclobutane containing $C_6F_{14}$ dissolved therein and $IF_5$. The contents of the reaction vessel 1 and the receiver 4 were analyzed by means of gas chromatography, as a result, it was found that the conversion of $C_6F_{13}I$ was 94% and the selectivity for $C_6F_{14}$ was 95%.

According to gas chromatography analysis of the uncondensed gas, no decomposition product was found.

What is claimed is:

1. A process for producing a perfluoroalkane corresponding to a general formula Rf-F (wherein Rf- is a perfluoroalkyl group represented by $F(CF_2)_n$— and n is an integer of 2 to 10), wherein a reaction:

$$Rf\text{-}I + 3F_2 \rightarrow Rf\text{-}F + IF_5 \tag{1}$$

is effected in the presence of at least one liquid selected from a perfluoro-compound, a chlorofluoro-compound, and hydrogen fluoride which liquid is substantially inert to the perfluoroalkyl iodide and gaseous fluorine and evaporates at least partially by heat generated by the reaction.

2. The process according to claim 1 wherein the evaporated compound is condensed by cooling and at least a part of the obtained condensate is evaporated by heat of subsequent reaction.

3. The process according to claim 1, wherein said liquid compound is selected from a group consisting of perfluoroethane, perfluoropropane, perfluorobutane, perfluorohexane, dichlorodifluoromethane, trichlorotrifluoroethane, fluorotrichloromethane, dichlorotetrafluoroethane, perfluorocyclobutane, perfluorocyclopentane, perfluorocyclohexane, perfluorodecalin, perfluorotributylamine, and perfluorotriethylamine.

4. The method according to claim 3, wherein said liquid compound has a boiling point in a range of −40° C. to 80° C.

5. The method according to claim 3, wherein said liquid compound has 1 to 15 carbon atoms.

6. The process according to claim 2, wherein n in the formula $F(CF_2)_n$— is 2 and perfluorocyclobutane and/or hydrogen fluoride is used as the liquid, or alternatively, n in the formula $F(CF_2)_n$— is 6 and perfluorohexane and/or hydrogen fluoride is used as the liquid.

7. A process for producing $IF_5$ characterized in that $IF_5$ is produced simultaneously in the process according to claim 1.

* * * * *